(12) United States Patent
Ferlita et al.

(10) Patent No.: US 7,612,072 B2
(45) Date of Patent: *Nov. 3, 2009

(54) AMORPHOUS FORM OF A PHOSPHORIC ACID SALT OF A DIPEPTIDYL PEPTIDASE-IV INHIBITOR

(75) Inventors: Russell R. Ferlita, Westfield, NJ (US); Robert M. Wenslow, Cream Ridge, NJ (US)

(73) Assignee: Merck & Co., Inc., Rahway, NJ (US)

( * ) Notice: Subject to any disclaimer, the term of this patent is extended or adjusted under 35 U.S.C. 154(b) by 335 days.

This patent is subject to a terminal disclaimer.

(21) Appl. No.: 11/660,722

(22) PCT Filed: Sep. 9, 2005

(86) PCT No.: PCT/US2005/032079

§ 371 (c)(1), (2), (4) Date: Feb. 20, 2007

(87) PCT Pub. No.: WO2006/033848

PCT Pub. Date: Mar. 30, 2006

(65) Prior Publication Data

US 2007/0281941 A1    Dec. 6, 2007

Related U.S. Application Data

(60) Provisional application No. 60/610,019, filed on Sep. 15, 2004.

(51) Int. Cl.
*A61K 31/4985* (2006.01)

(52) U.S. Cl. .................. 514/249; 544/350

(58) Field of Classification Search .................. 544/350
See application file for complete search history.

(56) References Cited

U.S. PATENT DOCUMENTS

| | | |
|---|---|---|
| 6,699,871 B2 | 3/2004 | Edmondson et al. |
| 2003/0100563 A1 | 5/2003 | Edmondson et al. |
| 2005/0032804 A1 | 2/2005 | Cypes et al. |
| 2006/0287528 A1 | 12/2006 | Wenslow et al. |
| 2007/0021430 A1 | 1/2007 | Chen et al. |

FOREIGN PATENT DOCUMENTS

| | | |
|---|---|---|
| WO | WO 03/004498 A1 | 1/2003 |
| WO | WO 2005/003135 A1 | 1/2005 |
| WO | WO 2005/020920 A2 | 3/2005 |
| WO | WO 2005/020920 A3 | 3/2005 |
| WO | WO 2005/030127 A2 | 4/2005 |
| WO | WO 2005/072530 A1 | 8/2005 |

*Primary Examiner*—James O Wilson
*Assistant Examiner*—Brian McDowell
(74) *Attorney, Agent, or Firm*—Philippe L. Durette; Catherine D. Fitch

(57) ABSTRACT

The present invention relates to a novel amorphous form of the dihydrogenphosphate salt of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine of structural formula I as well as a process for its preparation, pharmaceutical compositions containing this novel form, and methods of use of the novel form and pharmaceutical compositions for the treatment of diabetes, obesity, and high blood pressure.

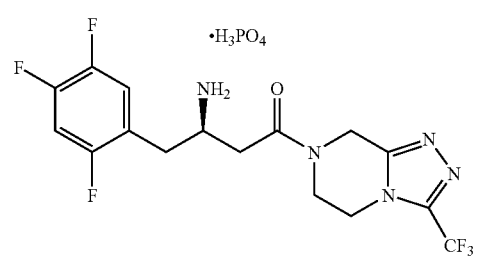

(I)

8 Claims, 5 Drawing Sheets

AMORPHOUS FORM OF A PHOSPHORIC ACID SALT OF A DIPEPTIDYL PEPTIDASE-IV INHIBITOR

CROSS REFERENCE TO RELATED APPLICATIONS

This application is the National Stage of International Application No. PCT/US2005/032079, filed 09 Sep. 2005, which claims the benefit under 35 U.S.C. 119(e) of U.S. Provisional Application No. 60/610,019, filed 15 Sep. 2004.

FIELD OF THE INVENTION

The present invention relates to a novel amorphous form of a dihydrogenphosphate salt of a dipeptidyl peptidase-IV (DPP-IV) inhibitor. More particularly, the invention relates to a novel amorphous form of the dihydrogenphosphate salt of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine, which is a potent inhibitor of DPP-IV. This novel amorphous form of the DPP-IV inhibitor is useful for the preparation of pharmaceutical compositions containing the inhibitor which are useful for the treatment and prevention of diseases and conditions for which an inhibitor of DPP-IV is indicated, in particular Type 2 diabetes, hyperglycemia, insulin resistance, obesity, and high blood pressure. The invention further concerns pharmaceutical compositions comprising the novel amorphous dihydrogenphosphate salt of the present invention; processes for preparing the amorphous dihydrogenphosphate salt and its pharmaceutical compositions; and methods of treating conditions for which a DPP-IV inhibitor is indicated comprising administering a composition of the present invention.

BACKGROUND OF THE INVENTION

Inhibition of dipeptidyl peptidase-IV (DPP-IV), an enzyme that inactivates both glucose-dependent insulinotropic peptide (GIP) and glucagon-like peptide 1 (GLP-1), represents a novel approach to the treatment and prevention of Type 2 diabetes, also known as non-insulin dependent diabetes mellitus (NIDDM). The therapeutic potential of DPP-IV inhibitors for the treatment of Type 2 diabetes has been reviewed: C. F. Deacon and J. J. Holst, "Dipeptidyl peptidase IV inhibition as an approach to the treatment and prevention of Type 2 diabetes: a historical perspective," *Biochem. Biophys. Res. Commun.*, 294: 1-4 (2000); K. Augustyns, et al., "Dipeptidyl peptidase IV inhibitors as new therapeutic agents for the treatment of Type 2 diabetes," *Exp. Opin. Ther. Patents*, 13: 499-510 (2003); D. J. Drucker, "Therapeutic potential of dipeptidyl peptidase IV inhibitors for the treatment of Type 2 diabetes," *Exp. Opin. Investig. Drugs*, 12: 87-100 (2003); and C. F. Deacon, et al., "Inhibitors of dipeptidyl peptidase IV: a novel approach for the prevention and treatment of Type 2 diabetes," *Exp. Opin. Investig. Drugs*, 13: 1091-1102 (2004).

U.S. Pat. No. 6,699,871 (issued Mar. 2, 2004), the contents of which are incorporated by reference herein in their entirety, describes a class of beta-amino tetrahydrotriazolo[4,3-α] pyrazines, which are potent inhibitors of DPP-IV useful for the treatment of Type 2 diabetes. Specifically disclosed in this U.S. patent is (2R)-4-oxo-4-[3-(trifluoromethyl)-5,6-dihydro [1,2,4]triazolo[4,3-α]pyrazin-7(8H)-yl]-1-(2,4,5-trifluorophenyl)butan-2-amine. However, there is no disclosure of the newly discovered amorphous form of the dihydrogenphosphate salt of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine of structural formula I below (hereinafter referred to as Compound I).

SUMMARY OF THE INVENTION

The present invention is concerned with a novel amorphous form of the dihydrogenphosphate salt of the DPP-IV inhibitor (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine of structural formula I (Compound I). The amorphous form of the present invention displays distinct dissolution characteristics relative to crystalline forms of the dihydrogenphosphate salt of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine which may have advantages in the preparation of certain pharmaceutical compositions of Compound I. Amorphous forms of Compound I may also exhibit distinct bioavailability and other pharmacokinetic characteristics compared to crystalline forms rendering them preferred forms for certain clinical applications. The present invention also concerns pharmaceutical compositions containing the novel amorphous form; processes for the preparation of this amorphous form and its pharmaceutical compositions; and methods for using them for the prevention or treatment of Type 2 diabetes, hyperglycemia, insulin resistance, obesity, and high blood pressure.

DETAILED DESCRIPTION OF THE INVENTION

Text The present invention provides (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine (Compound I) in an amorphous form.

X-ray powder diffraction studies are widely used to characterize molecular structures, crystallinity, and polymorphism. The X-ray powder diffraction pattern of the amorphous Compound I was generated on a Philips Analytical X'Pert PRO X-ray Diffraction System with PW3040/60 console. A PW3373/00 ceramic Cu LEF X-ray tube K-Alpha radiation was used as the source.

Figure 1:
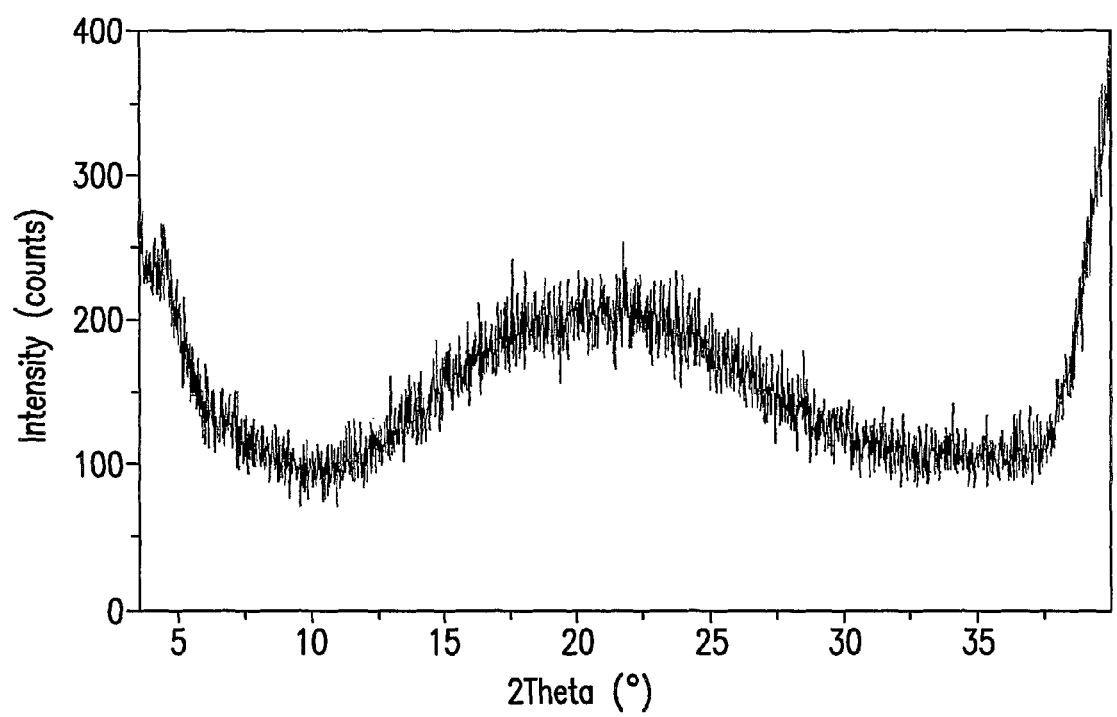
FIG. 1 is a characteristic X-ray diffraction pattern of the amorphous Compound I of the present invention.

FIG. 1 shows the X-ray diffraction pattern for amorphous Compound I. The pattern for the amorphous Compound I is characterized by broad diffuse halos having very low counts with no distinctive absorption bands in contrast to sharp peaks typically observed with crystalline materials.

In addition to the X-ray powder diffraction patterns described above, the amorphous form of Compound I was further characterized by its solid-state carbon-13 and fluorine-19 nuclear magnetic resonance (NMR) spectra. The solid-state carbon-13 NMR spectrum was obtained on a Bruker DSX 400WB NMR system using a Bruker 4 mm double resonance CPMAS probe. The carbon-13 NMR spectrum utilized proton/carbon-13 cross-polarization magic-angle spinning with variable-amplitude cross polarization. The sample was spun at 15.0 kHz, and a total of 1024 scans were collected with a recycle delay of 5 seconds. A line broadening of 40 Hz was applied to the spectrum before FT was performed. Chemical shifts are reported on the TMS scale using the carbonyl carbon of glycine (176.03 p.p.m.) as a secondary reference.

The solid-state fluorine-19 NMR spectrum was obtained on a Bruker DSX 400WB NMR system using a Bruker 4 mm CRAMPS probe. The NMR spectrum utilized a simple pulse-acquire pulse program. The samples were spun at 15.0 kHz, and a total of 128 scans were collected with a recycle delay of 5 seconds. A vespel endcap was utilized to minimize fluorine background. A line broadening of 100 Hz was applied to the spectrum before FT was performed. Chemical shifts are reported using poly(tetrafluoroethylene) (teflon) as an external secondary reference which was assigned a chemical shift of −122 p.p.m.

DSC data were acquired using TA Instruments DSC 2910 or equivalent instrumentation is used. Between 2 and 6 mg sample is weighed into an open pan. This pan is then crimped and placed at the sample position in the calorimeter cell. An empty pan is placed at the reference position. The calorimeter cell is closed and a flow of nitrogen is passed through the cell. The heating program is set to heat the sample at a heating rate of 10° C./min to a temperature of approximately 250° C. The heating program is started. When the run is completed, the data are analyzed using the DSC analysis program contained in the system software. The melting endotherm is integrated between baseline temperature points that are above and below the temperature range over which the endotherm is observed. The data reported are the onset temperature, peak temperature and enthalpy.

TG data were acquired using a Perkin Elmer model TGA 7. Experiments were performed under a flow of nitrogen and using a heating rate of 10° C./min to a maximum temperature of approximately 250° C. After automatically taring the balance, 5 to 20 mg of sample was added to the platinum pan, the furnace was raised, and the heating program started. Weight/temperature data were collected automatically by the instrument. Analysis of the results was carried out by selecting the Delta Y function within the instrument software and choosing the temperatures between which the weight loss was to be calculated. Weight losses are reported up to the onset of decomposition/evaporation.

Figure 2:
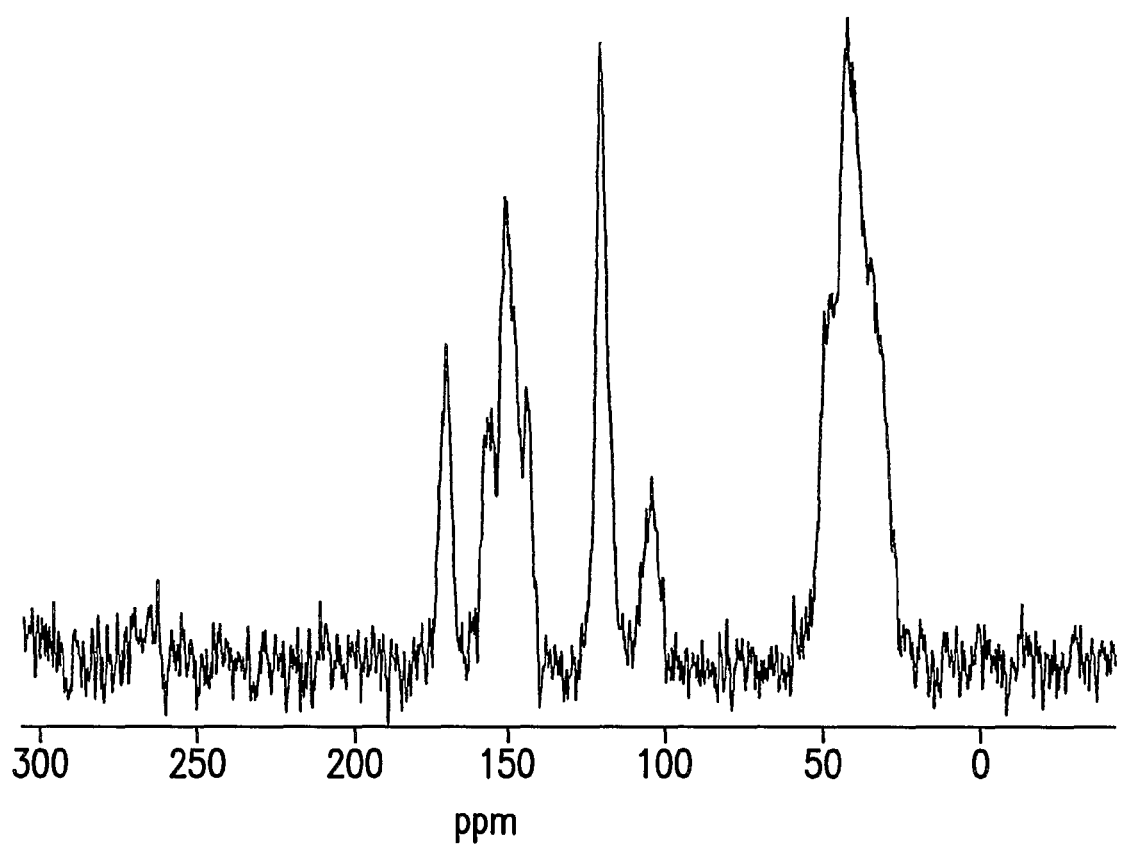
FIG. 2 is a fluorine-19 magic-angle spinning (MAS) nuclear magnetic resonance (NMR) spectrum of the amorphous Compound I of the present invention.

FIG. 2 shows the solid-state carbon-13 CPMAS NMR spectrum for amorphous Compound I. Amorphous Compound I exhibited characteristic signals with chemical shift values of 169.6, 150.6, 120.1, and 41.9 p.p.m.

Figure 3:
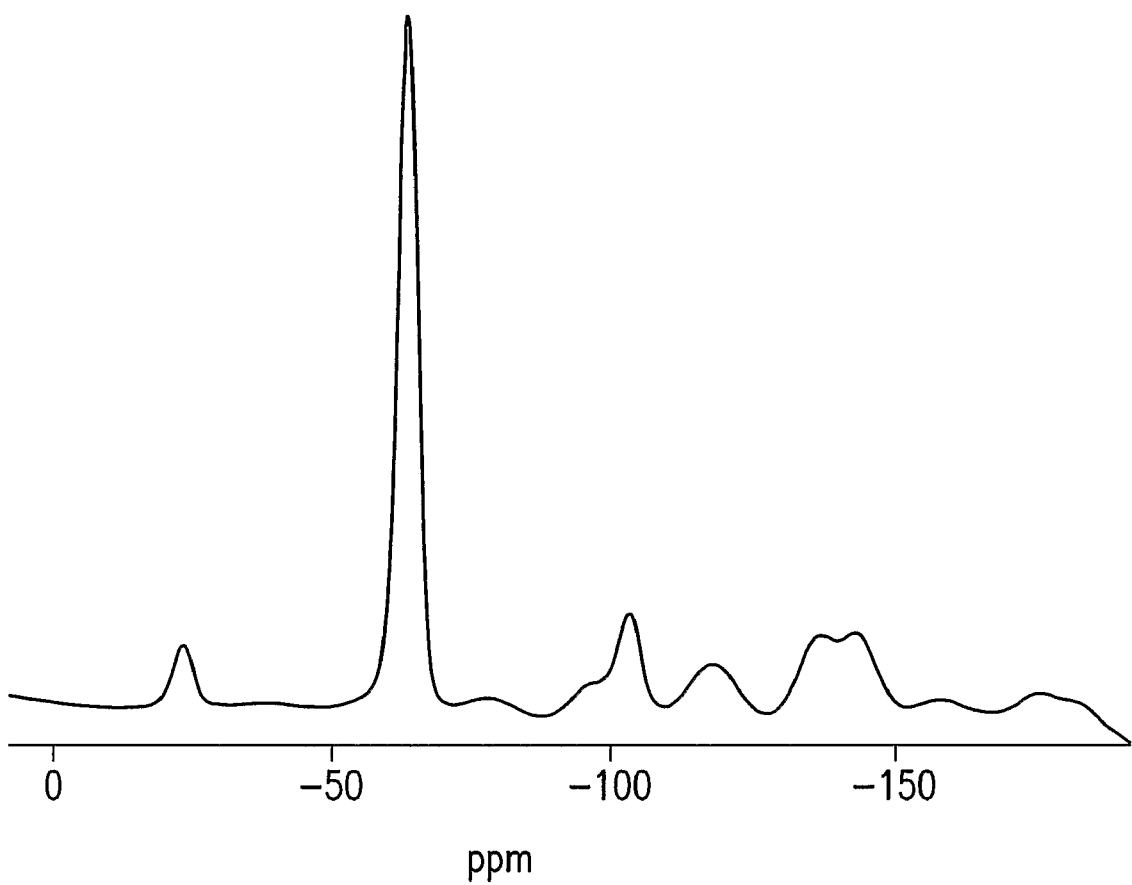
FIG. 3 is a carbon-13 cross-polarization magic-angle spinning (CPMAS) nuclear magnetic resonance (NMR) spectrum of the amorphous Compound I of the present invention.

FIG. 3 shows the solid-state fluorine-19 MAS NMR spectrum for amorphous Compound I. Amorphous Compound I exhibited characteristic signals with chemical shift values of −63.7, −118.5, −136.6, and −143.3 p.p.m.

Figure 4:
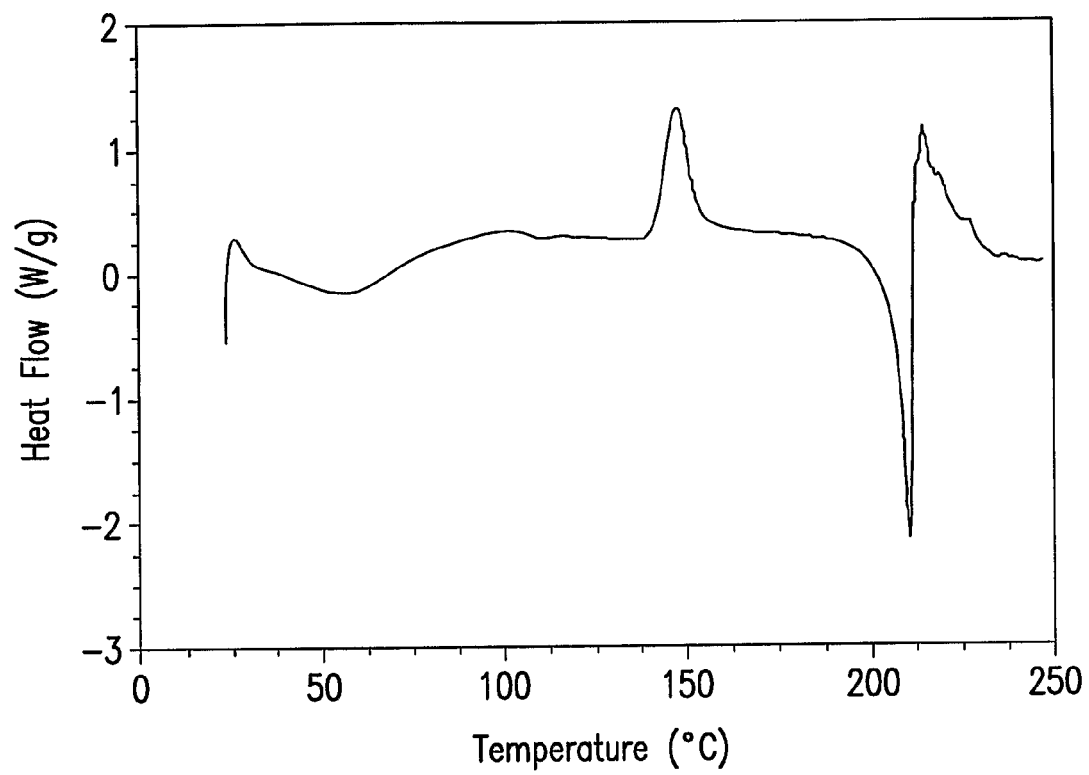
FIG. 4 is a typical DSC curve of the amorphous Compound I of the present invention.

FIG. 4 shows a characteristic DSC curve for amorphous Compound I. The broad endotherm up to approximately 90° C. is the loss of the adsorbed water. The step transition at approximately 105° C. is due to the glass transition of the material. The exotherm at approximately 140° C. is the crystallization of the material to anhydrous Form I. The endotherm at approximately 190° C. is the melt of Form I.

Figure 5:
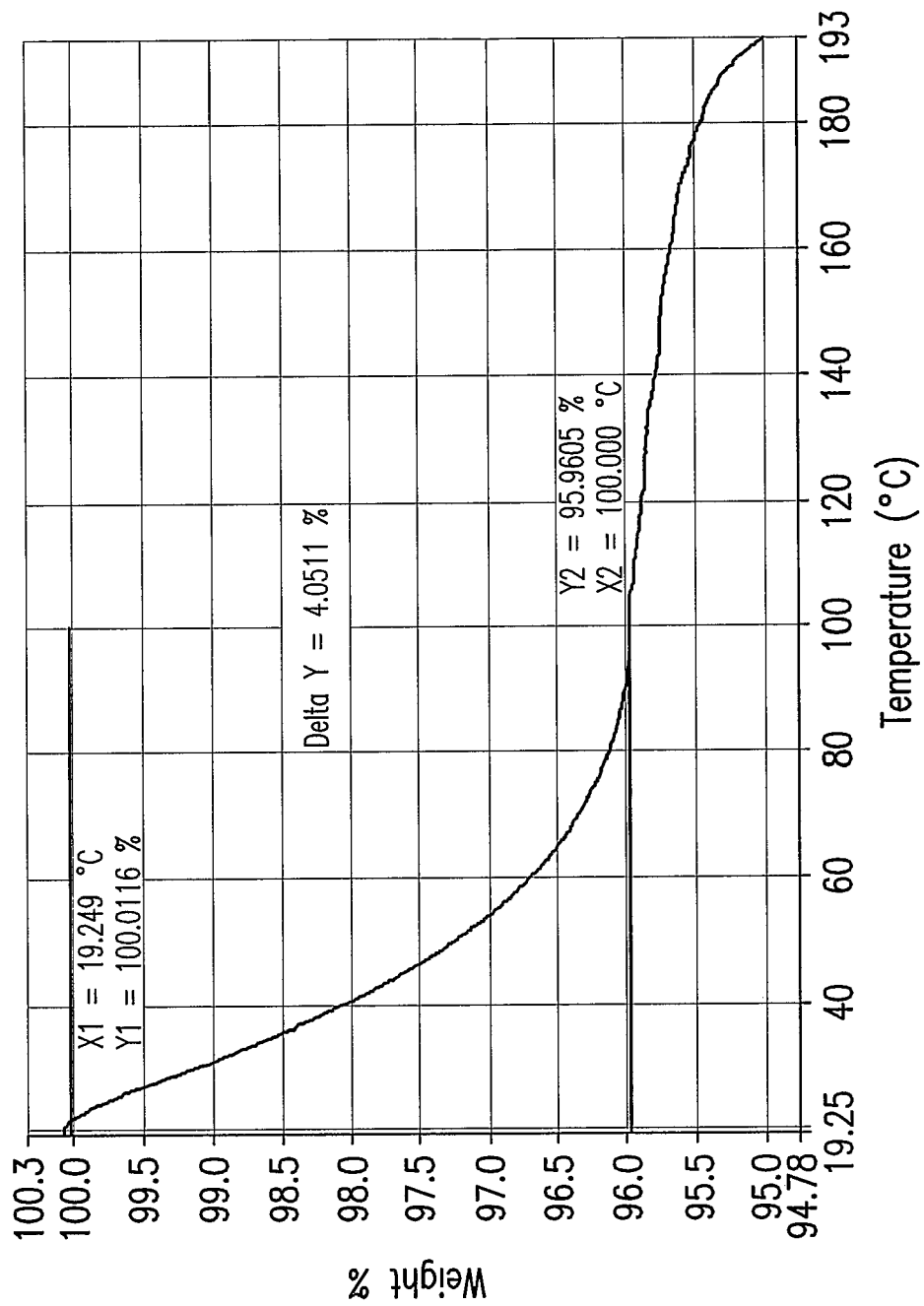
FIG. 5 is a typical TG curve of the amorphous Compound I of the present invention.

FIG. 5 shows a characteristic thermogravimetric analysis (TGA) curve for amorphous Compound I. The initial weight loss on the TGA is due to adsorbed water on the amorphous material.

Another aspect of the present invention provides the Compound I drug substance that comprises the amorphous form in a detectable amount. By "drug substance" is meant the active pharmaceutical ingredient (API). The amount of the amorphous form in the drug substance can be quantified by the use of physical methods such as X-ray powder diffraction, solid-state fluorine-19 magic-angle spinning (MAS) nuclear magnetic resonance spectroscopy, solid-state carbon-13 cross-polarization magic-angle spinning (CPMAS) nuclear magnetic resonance spectroscopy, solid state Fourier-transform infrared spectroscopy, and Raman spectroscopy. A detectable amount is an amount that can be detected by such physical methods. The limits of detection of such methods is anticipated to improve with technological advances. The remainder of the drug substance may additionally comprise various crystalline forms of Compound I and polymorphs and pseudopolymorphs thereof. In a class of this embodiment, about 5% to about 100% by weight of the amorphous form is present in the drug substance. In a second class of this embodiment, about 10% to about 100% by weight of the amorphous form is present in the drug substance. In a third class of this embodiment, about 25% to about 100% by weight of the amorphous form is present in the drug substance. In a fourth class of this embodiment, about 50% to about 100% by weight of the amorphous form is present in the drug substance. In a fifth class of this embodiment, about 75% to about 100% by weight of the amorphous form is present in the drug substance. In a sixth class of this embodiment, substantially all of the Compound I drug substance is the amorphous form, i.e., the Compound I drug substance is substantially phase pure amorphous form.

Another aspect of the present invention provides a method for the prevention or treatment of clinical conditions for which an inhibitor of DPP-IV is indicated, which method comprises administering to a patient in need of such prevention or treatment a prophylactically or therapeutically effective amount of the amorphous form of Compound I. Such clinical conditions include diabetes, in particular Type 2 diabetes, hyperglycemia, insulin resistance, obesity, and high blood pressure.

The present invention also provides for the use of the amorphous Compound I of the present invention in the manufacture of a medicament for the prevention or treatment of clinical conditions for which an inhibitor of DPP-IV is indicated, in particular, Type 2 diabetes, hyperglycemia, insulin resistance, obesity, and high blood pressure. In one embodiment the clinical condition is Type 2 diabetes.

Another aspect of the present invention provides the amorphous Compound I for use in the treatment of clinical conditions for which an inhibitor of DPP-IV is indicated, in particular, Type 2 diabetes, hyperglycemia, insulin resistance, obesity, and high blood pressure. In one embodiment of this aspect the clinical condition is Type 2 diabetes.

The present invention also provides pharmaceutical compositions comprising the amorphous Compound I, in association with one or more pharmaceutically acceptable carriers or excipients. In one embodiment the pharmaceutical composition comprises a prophylactically or therapeutically effective amount of the active pharmaceutical ingredient (API) in admixture with pharmaceutically acceptable excipients wherein the API comprises a detectable amount of the amorphous form of the present invention. In a second embodiment the pharmaceutical composition comprises a prophylactically or therapeutically effective amount of the API in admixture with pharmaceutically acceptable excipients wherein the API comprises about 5% to about 100% by weight of amorphous Compound I of the present invention. In a class of this second embodiment, the API in such compositions comprises about 10% to about 100% by weight of amorphous Compound I. In a second class of this embodiment, the API in such compositions comprises about 25% to about 100% by weight of amorphous Compound I. In a third class of this embodiment, the API in such compositions comprises about 50% to about 100% by weight of amorphous Compound I. In a fourth class of this embodiment, the API in such compositions comprises about 75% to about 100% by weight of amorphous Compound I. In a fifth class of this embodiment, substantially all of the API is amorphous Compound I, i.e., the API is substantially phase pure amorphous Compound I. When not comprising substantially phase pure amorphous Compound I, such compositions may additionally comprise various crystalline forms of Compound I and polymorphs and pseudopolymorphs thereof.

The compositions in accordance with the invention are suitably in unit dosage forms such as tablets, pills, capsules, powders, granules, sterile solutions or suspensions, metered aerosol or liquid sprays, drops, ampoules, auto-injector devices or suppositories. The compositions are intended for oral, parenteral, intranasal, sublingual, or rectal administration, or for administration by inhalation or insufflation. Formulation of the compositions according to the invention can conveniently be effected by methods known from the art, for example, as described in *Remington's Pharmaceutical Sciences*, 17$^{th}$ ed., 1995.

The dosage regimen is selected in accordance with a variety of factors including type, species, age, weight, sex and medical condition of the patient; the severity of the condition to be treated; the route of administration; and the renal and hepatic function of the patient. An ordinarily skilled physician, veterinarian, or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the API for the symptomatic adjustment of the dosage to the patient to be treated. A medicament typically contains from about 0.01 mg to about 500 mg of the API, preferably, from about 1 mg to about 200 mg of API. Intravenously, the most preferred doses will range from about 0.1 to about 10 mg/kg/minute during a constant rate infusion. Advantageously, the amorphous Compound I of the present invention may be administered in a single daily dose, or the total daily dosage may be administered in divided doses of two, three or four times daily. Furthermore, the amorphous form of the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

In the methods of the present invention, the amorphous Compound I herein described in detail can form the API, and is typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active pharmaceutical ingredient can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral API can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The amorphous form of Compound I has been found to possess a high solubility in water, rendering it especially amenable to the preparation of formulations, in particular intranasal and intravenous formulations, which require relatively concentrated aqueous solutions of the API.

The pharmaceutical compositions of the present invention may include one or more additional agents useful for the treatment of Type 2 diabetes, such as metformin; a sulfonylurea, such as glipizide, glyburide, and glimepiride; a PPARγ agonist, such as pioglitazone and rosiglitazone; and a PPARα/γ dual agonist, such as muraglitazar.

In a still further aspect, the present invention provides a method for the treatment and/or prevention of clinical conditions for which a DPP-IV inhibitor is indicated, which method comprises administering to a patient in need of such prevention or treatment a prophylactically or therapeutically effective amount of amorphous Compound I of the present invention or a pharmaceutical composition containing a prophylactically or therapeutically effective amount of amorphous Compound I.

The following non-limiting Examples are intended to illustrate the present invention and should not be construed as being limitations on the scope or spirit of the instant invention.

Compounds described herein may exist as tautomers such as keto-enol tautomers. The individual tautomers as well as mixtures thereof are encompassed with compounds of structural formula I.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

EXAMPLE

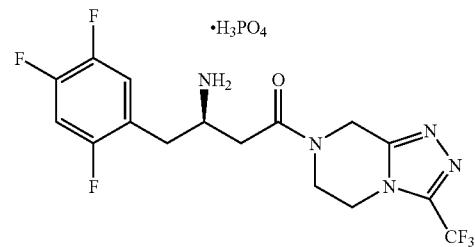

Preparation of Amorphous Form of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine dihydrogenphosphate Preparation of 3-(trifluoromethyl)-5,6,7,8-tetrahydro[1,2,4]triazolo[4,3-α]pyrazine hydrochloride (1-4)

Scheme 1

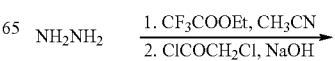

-continued

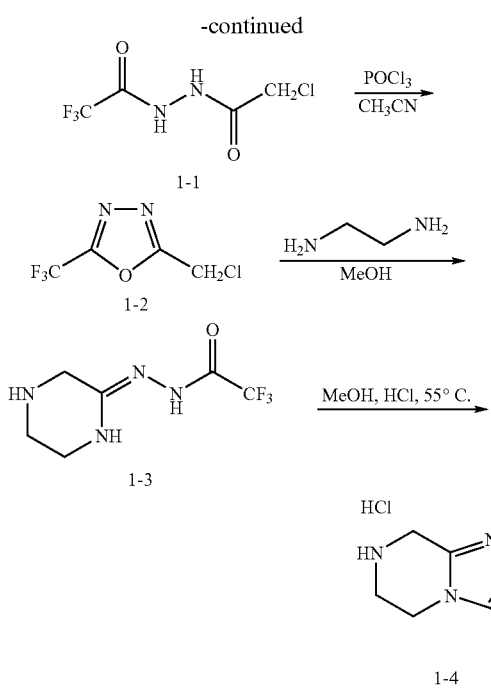

Step A

Preparation of Bishydrazide (1-1)

Hydrazine (20.1 g, 35 wt % in water, 0.22 mol) was mixed with 310 mL of acetonitrile. 31.5 g of ethyl trifluoroacetate (0.22 mol) was added over 60 min. The internal temperature was increased to 25° C. from 14° C. The resulting solution was aged at 22-25° C. for 60 min. The solution was cooled to 7° C. 17.9 g of 50 wt % aqueous NaOH (0.22 mol) and 25.3 g of chloroacetyl chloride (0.22 mol) were added simultaneously over 130 min at a temperature below 16° C. When the reaction was complete, the mixture was vacuum distilled to remove water and ethanol at 27~30° C. and under 26~27 in Hg vacuum. During the distillation, 720 mL of acetonitrile was added slowly to maintain constant volume (approximately 500 mL). The slurry was filtered to remove sodium chloride. The cake was rinsed with about 100 mL of acetonitrile. Removal of the solvent afforded bis-hydrazide 1-1 (43.2 g, 96.5% yield, 94.4 area % pure by HPLC assay).

$^1$H-NMR (400 MHz, DMSO-d$_6$): δ 4.2 (s, 2H), 10.7 (s, 1H), and 11.6 (s, 1H) p.p.m.

$^{13}$C-NMR (100 MHz, DMSO-d$_6$): δ 41.0, 116.1 (q, J=362 Hz), 155.8 (q, J=50 Hz), and 165.4 p.p.m.

Step B

Preparation of 5-(trifluoromethyl)-2-(chloromethyl)-1,3,4-oxadiazole (1-2)

Bishydrazide 1-1 from Step A (43.2 g, 0.21 mol) in ACN (82 mL) was cooled to 5° C. Phosphorus oxychloride (32.2 g, 0.21 mol) was added, maintaining the temperature below 10° C. The mixture was heated to 80° C. and aged at this temperature for 24 h until HPLC showed less than 2 area % of 1-1. In a separate vessel, 260 mL of IPAc and 250 mL of water were mixed and cooled to 0° C. The reaction slurry was charged to the quench keeping the internal temperature below 10° C. After the addition, the mixture was agitated vigorously for 30 min, the temperature was increased to room temperature and the aqueous layer was cut. The organic layer was then washed with 215 mL of water, 215 mL of 5 wt % aqueous sodium bicarbonate and finally 215 mL of 20 wt % aqueous brine solution. HPLC assay yield after work up was 86-92%. Volatiles were removed by distillation at 75-80 mm Hg, 55° C. to afford an oil which could be used directly in Step C without further purification. Otherwise the product can be purified by distillation to afford 1-2 in 70-80% yield.

$^1$H-NMR (400 MHz, CDCl$_3$): δ 4.8 (s, 2H) p.p.m.

$^{13}$C-NMR (100 MHz, CDCl$_3$): δ 32.1, 115.8 (q, J=337 Hz), 156.2 (q, J=50 Hz), and 164.4 p.p.m.

Step C

Preparation of N-[(2Z)-piperazin-2-ylidene]trifluoro-acetohydrazide (1-3)

To a solution of ethylenediamine (33.1 g, 0.55 mol) in methanol (150 mL) cooled at −20° C. was added distilled oxadiazole 1-2 from Step B (29.8 g, 0.16 mol) while keeping the internal temperature at −20° C. After the addition was complete, the resulting slurry was aged at −20° C. for 1 h. Ethanol (225 mL) was then charged and the slurry slowly warmed to −5° C. After 60 min at −5° C., the slurry was filtered and washed with ethanol (60 mL) at −5° C. Amidine 1-3 was obtained as a white solid in 72% yield (24.4 g, 99.5 area wt % pure by HPLC).

$^1$H-NMR (400 MHz, DMSO-d$_6$): δ 2.9 (t, 2H), 3.2 (t, 2H), 3.6 (s, 2H), and 8.3 (b, 1H) p.p.m. $^{13}$C-NMR (100 MHz, DMSO-d$_6$): δ 40.8, 42.0, 43.3, 119.3 (q, J=350 Hz), 154.2, and 156.2 (q, J=38 Hz) p.p.m.

Step D

Preparation of 3-(trifluoromethyl)-5,6,7,8-tetrahydro [1,2,4]triazolo[4,3-α]pyrazine hydrochloride (1-4)

A suspension of amidine 1-3 (27.3 g, 0.13 mol) in 110 mL of methanol was warmed to 55° C. 37% Hydrochloric acid (11.2 mL, 0.14 mol) was added over 15 min at this temperature. During the addition, all solids dissolved resulting in a clear solution. The reaction was aged for 30 min. The solution was cooled down to 20° C. and aged at this temperature until a seed bed formed (10 min to 1 h). 300 mL of MTBE was charged at 20° C. over 1 h. The resulting slurry was cooled to 2° C., aged for 30 min and filtered. Solids were washed with 50 mL of ethanol:MTBE (1:3) and dried under vacuum at 45° C. Yield of triazole 1-4 was 26.7 g (99.5 area wt % pure by HPLC).

$^1$H-NMR (400 MHz, DMSO-d$_6$): δ 3.6 (t, 2H), 4.4 (t, 2H), 4.6 (s, 2H), and 10.6 (b, 2H) p.p.m.; $^{13}$C-NMR (100 MHz, DMSO-d$_6$): δ: 39.4, 39.6, 41.0, 118.6 (q, J=325 Hz), 142.9 (q, J=50 Hz), and 148.8 p.p.m.

Scheme 2

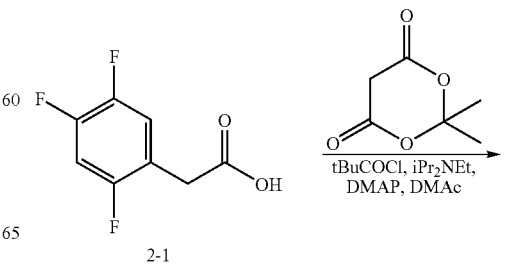

-continued

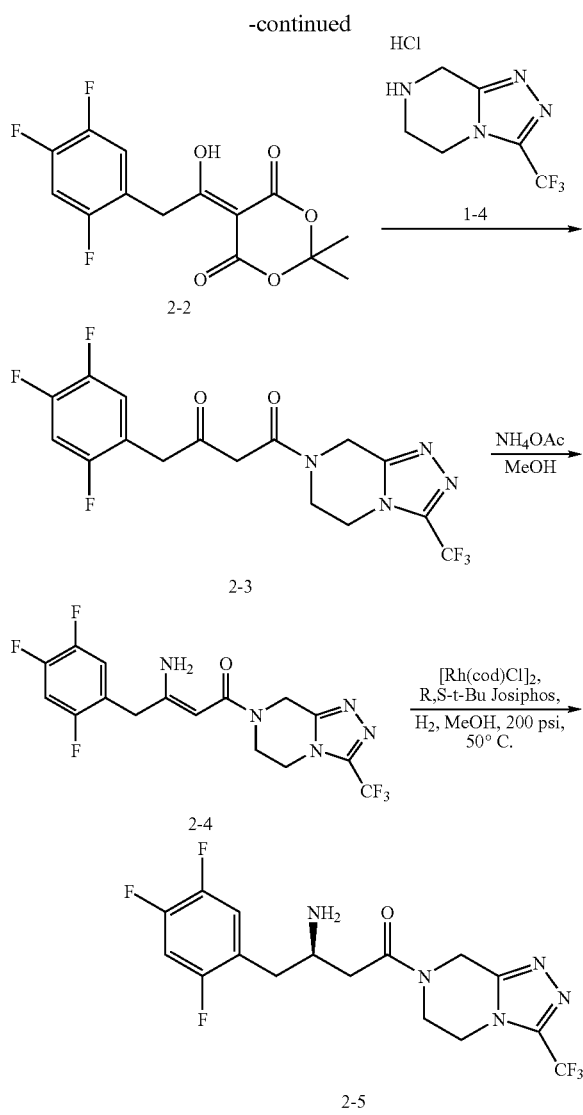

Step A

Preparation of 4-oxo-4-[3-(trifluoromethyl)-5,6-dihydro[1,2,4]triazolo[4,3-α]pyrazin-7(8H)-yl]-1-(2,4,5-trifluorophenyl)butan-2-one (2-3)

2,4,5-Trifluorophenylacetic acid (2-1) (150 g, 0.789 mol), Meldrum's acid (125 g, 0.868 mol), and 4-(dimethylamino)pyridine (DMAP) (7.7 g, 0063 mol) were charged into a 5 L three-neck flask. N,N-Dimethylacetamide (Mac) (525 mL) was added in one portion at room temperature to dissolve the solids. N,N-diisopropylethylamine (282 mL, 1.62 mol) was added in one portion at room temperature while maintaining the temperature below 40° C. Pivaloyl chloride (107 mL, 0.868 mol) was added dropwise over 1 to 2 h while maintaining the temperature between 0 and 5° C. The reaction mixture was aged at 5° C. for 1 h. Triazole hydrochloride 1-4 (180 g, 0.789 mol) was added in one portion at 40-50° C. The reaction solution was aged at 70° C. for several h. 5% Aqueous sodium hydrogencarbonate solution (625 mL) was then added dropwise at 20-45° C. The batch was seeded and aged at 20-30° C. for 1-2 h. Then an additional 525 mL of 5% aqueous sodium hydrogencarbonate solution was added dropwise over 2-3 h. After aging several h at room temperature, the slurry was cooled to 0-5° C. and aged 1 h before filtering the solid. The wet cake was displacement-washed with 20% aqueous Mac (300 mL), followed by an additional two batches of 20% aqueous Mac (400 mL), and finally water (400 mL). The cake was suction-dried at room temperature. The isolated yield of final product 2-3 was 89%.

Step B

Preparation of (2Z)-4-oxo-4-[3-(trifluoromethyl)-5,6-dihydro[1,2,4]triazolo[4,3-α]pyrazin-7(8H)-yl]-1-(2,4,5-trifluorophenyl)but-2-en-2-amine (2-4)

A 5 L round-bottom flask was charged with methanol (100 mL), the ketoamide 2-3 (200 g), and ammonium acetate (110.4 g). Methanol (180 mL) and 28% aqueous ammonium hydroxide (58.6 mL) were then added keeping the temperature below 30° C. during the addition. Additional methanol (100 mL) was added to the reaction mixture. The mixture was heated at reflux temperature and aged for 2 h. The reaction was cooled to room temperature and then to about 5° C. in an ice-bath. After 30 min, the solid was filtered and dried to afford 2-4 as a solid (180 g); m.p. 271.2° C.

Step C

Preparation of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine (2-5)

Into a 500 ml flask were charged chloro(1,5-cyclooctadiene)rhodium(I) dimer {[Rh(cod)Cl]$_2$} (292 mg, 1.18 mmol) and (R,S) t-butyl Josiphos (708 mg, 1.3 mmol) under a nitrogen atmosphere. Degassed MeOH was then added (200 mL) and the mixture was stirred at room temperature for 1 h. Into a 4 L hydrogenator was charged the enamine amide 2-4 (118 g, 0.29 mol) along with MeOH (1 L). The slurry was degassed. The catalyst solution was then transferred to the hydrogenator under nitrogen. After degassing three times, the enamine amide was hydrogenated under 200 psi hydrogen gas at 50° C. for 13 h. Assay yield was determined by HPLC to be 93% and optical purity to be 94% ee.

The optical purity was further enhanced in the following manner. The methanol solution from the hydrogenation reaction (18 g in 180 mL MeOH) was concentrated and switched to methyl t-butyl ether (MTBE) (45 mL). Into this solution was added aqueous H$_3$PO$_4$ solution (0.5 M, 95 mL). After separation of the layers, 3N NaOH (35 mL) was added to the water layer, which was then extracted with MTBE (180 mL+100 mL). The MTBE solution was concentrated and solvent switched to hot toluene (180 mL, about 75° C). The hot toluene solution was then allowed to cool to 0° C. slowly (5-10 h). The crystals were isolated by filtration (13 g, yield 72%, 98-99% ee); m.p. 114.1-115.7° C.

$^1$H NMR (300 MHz, CD$_3$CN): δ 7.26 (m), 7.08 (m), 4.90 (s), 4.89 (s), 4.14 (m), 3.95 (m), 3.40 (m), 2.68 (m), 2.49 (m), 1.40 (bs).

Compound 2-5 exists as amide bond rotamers. Unless indicated, the major and minor rotamers are grouped together since the carbon-13 signals are not well resolved:

$^{13}$C NMR (CD$_3$CN): δ 171.8, 157.4 (ddd, J$_{CF}$=242.4, 9.2, 2.5 Hz), 152.2 (major), 151.8 (minor), 149.3 (ddd; J$_{CF}$=246.7, 14.2, 12.9 Hz), 147.4 (ddd, J$_{CF}$=241.2, 12.3, 3.7 Hz), 144.2 (q, J$_{CF}$=38.8 Hz), 124.6 (ddd, J$_{CF}$=18.5, 5.9, 4.0 Hz), 120.4 (dd, J$_{CF}$=19.1, 6.2 Hz), 119.8 (q, J$_{CF}$=268.9 Hz), 106.2 (dd, J$_{CF}$=29.5, 20.9 Hz), 50.1, 44.8, 44.3 (minor), 43.2 (minor), 42.4, 41.6 (minor), 41.4, 39.6, 38.5 (minor), 36.9.

The crystalline free base 2-5 can also be isolated as follows:

(a) The reaction mixture upon completion of the hydrogenation step is charged with 25 wt % of Ecosorb C-941. The mixture is stirred under nitrogen for one h and then filtered. The cake is washed with 2 L/kg of methanol. Recovery of free base is about 95% and optical purity about 95% ee.
(b) The freebase solution in methanol is concentrated to 3.5-4.0 L/kg volume (based on free base charge) and then solvent-switched into isopropanol (IPA) to final volume of 3.0 L/kg IPA.
(c) The slurry is heated to 40° C. and aged 1 h at 40° C. and then cooled to 25° C. over 2 h.
(d) Heptane (7 L/kg) is charged over 7 h and the slurry stirred for 12 h at 22-25° C. The supernatant concentration before filtering is 10-12 mg/g.
(e) The slurry is filtered and the solid washed with 30% IPA/heptane (2 L/kg).
(f) The solid is dried in a vacuum oven at 40° C.
(g) The optical purity of the free base is about 99% ee.

The following high-performance liquid chromatographic (HPLC) conditions were used to determine percent conversion to product:

| | |
|---|---|
| Column: | Waters Symmetry C18, 250 mm × 4.6 mm |
| Eluent: | Solvent A: 0.1 vol % HClO$_4$/H$_2$O |
| | Solvent B: acetonitrile |
| Gradient: | 0 min 75% A: 25% B |
| | 10 min 25% A: 75% B |
| | 12.5 min 25% A: 75% B |
| | 15 min 75% A: 25% B |
| Flow rate: | 1 mL/min |
| Injection Vol.: | 10 µL |
| UV detection: | 210 nm |
| Column temp.: | 40° C. |
| Retention times: | compound 2-4: 9.1 min |
| | compound 2-5: 5.4 min |
| | tBu Josiphos: 8.7 min |

The following high-performance liquid chromatographic (HPLC) conditions were used to determine optical purity:

| | |
|---|---|
| Column: | Chirapak, AD-H, 250 mm × 4.6 mm |
| Eluent: | Solvent A: 0.2 vol. % diethylamine in heptane |
| | Solvent B: 0.1 vol % diethylamine in ethanol |
| Isochratic Run Time: | 18 min |
| Flow rate: | 0.7 mL/min |
| Injection Vol.: | 7 µL |
| UV detection: | 268 nm |
| Column temp.: | 35° C. |
| Retention times: | (R)-amine 2-5: 13.8 min |
| | (S)-amine 2-5: 11.2 min |

Preparation of Crystalline (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine dihydrogenphosphate monohydrate A 250 mL round bottom flask equipped with an overhead stirrer, heating mantle and thermocouple, was charged with 31.5 mL of isopropanol (IPA), 13.5 mL water, 15.0 g (36.9 mmol) of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine freebase and 4.25 g (36.9 mmol) of 85% aqueous phosphoric acid. The mixture was heated to 75° C. A thick white precipitate formed at lower temperatures but dissolved upon reaching 75° C. The solution was cooled to 68° C. and then held at that temperature for 2 h. A slurry bed of solids formed during this age time [the solution can be seeded with 0.5 to 5 wt % of small particle size (alpine milled) monohydrate]. The slurry was then cooled at a rate of 4° C./h to 21° C. and then held overnight. 105 mL of IPA was then added to the slurry. After 1 h the slurry was filtered and washed with 45 mL EPA. The solids were dried on the frit with open to air. The solids were found to greater than 99.8% pure by HPLC area percentage (HPLC conditions same as those given above).

Preparation of Amorphous (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine dihydrogenphosphate The above crystalline monohydrate was dissolved in water at a concentration of approximately 50 mg/mL. The mixture was agitated until no solid material was apparent, and the solution was filtered through a 0.2 µm filter into a clean container. The solution was then frozen using a dry ice/methanol bath. The sample was pulled under vacuum to remove the solvent and leave a fluffy, white amorphous solid. The solid displays no reflections when analyzed be X-ray powder diffraction.

Example of a Pharmaceutical Composition:

Amorphous Compound I (API) is formulated into a tablet by a direct compression process. A 100 mg potency tablet is composed of 124 mg of the API, 130 mg microcrystalline cellulose, 130 mg of mannitol (or 130 mg of dicalcium phosphate), 8 mg of croscarmellose sodium, 8 mg of magnesium stearate and 16 mg of Opadry white (proprietary coating material made by Colorcon, West Point, Pa.). The API, microcrystalline cellulose, mannitol (or dicalcium phosphate), and croscarmellose sodium are first blended, and the mixture is then lubricated with magnesium stearate and pressed into tablets. The tablets are then film coated with Opadry White.

What is claimed is:

1. An amorphous form of the dihydrogenphosphate salt of (2R)-4-oxo-4-[3-(trifluoromethyl)-5,6-dihydro[1,2,4]triazolo[4,3-α]pyrazin-7(8H)-yl]-1-(2,4,5-trifluorophenyl)butan-2-amine of structural formula I:

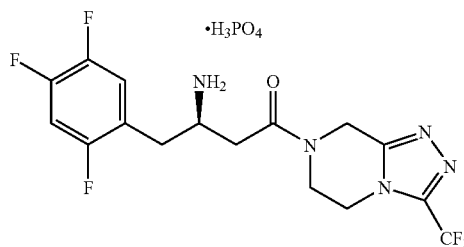

(I)

characterized by the X-ray powder diffraction pattern of FIG. 1.

2. The amorphous form of claim 1 characterized by a solid-state fluorine-19 magic-angle spinning (MAS) nuclear magnetic resonance spectrum showing signals at −63.7, −118.5, −136.6, and −143.3 p.p.m.

3. The amorphous form of claim 1 further characterized by the solid-state fluorine-19 magic-angle spinning (MAS) nuclear magnetic resonance spectrum of FIG. 3.

4. The amorphous form of claim 1 characterized by a solid-state carbon-13 cross-polarization magic-angle spinning (CPMAS) nuclear magnetic resonance spectrum showing signals at 169.6, 150.6, 120.1, and 41.9 p.p.m.

5. The amorphous form of claim 4 further characterized by the solid-state carbon-13 cross-polarization magic-angle spinning (CPMAS) nuclear magnetic resonance spectrum of FIG. 2.

6. The amorphous form of claim 1 characterized by the thermogravimetric analysis curve of FIG. 5.

7. The amorphous form of claim 1 characterized by the differential scanning calorimetric (DSC) curve of FIG. 4.

8. A pharmaceutical composition in solid form comprising a therapeutically effective amount of the amorphous form of claim 1 in association with one or more pharmaceutically acceptable carriers or excipients.

* * * * *

UNITED STATES PATENT AND TRADEMARK OFFICE
CERTIFICATE OF CORRECTION

PATENT NO.        : 7,612,072 B2
APPLICATION NO.   : 11/660722
DATED             : November 3, 2009
INVENTOR(S)       : Russell R. Ferlita and Robert M. Wenslow It is certified that error appears in the above-identified patent and that said Letters Patent is hereby corrected as shown below:

Claim 3, Line 61, Cancel "claim 1" and substitute therefor -- claim 3 --.

Signed and Sealed this

Twenty-second Day of December, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,612,072 B2 | Page 1 of 1 |
| APPLICATION NO. | : 11/660722 | |
| DATED | : November 3, 2009 | |
| INVENTOR(S) | : Russell R. Ferlita and Robert M. Wenslow | |

It is certified that error appears in the above-identified patent and that said Letters Patent is hereby corrected as shown below:

Column 12, Claim 3, Line 61, Cancel "claim 1" and substitute therefor -- claim 3 --.

This certificate supersedes the Certificate of Correction issued December 22, 2009.

Signed and Sealed this

Twelfth Day of January, 2010

David J. Kappos
*Director of the United States Patent and Trademark Office*